United States Patent
Itou

(10) Patent No.: US 11,226,387 B2
(45) Date of Patent: Jan. 18, 2022

(54) MAGNETIC RESONANCE IMAGING APPARATUS AND IMAGE PROCESSING APPARATUS

(71) Applicant: Hitachi, Ltd., Tokyo (JP)

(72) Inventor: Kousuke Itou, Tokyo (JP)

(73) Assignee: HITACHI, LTD., Tokyo (JP)

( * ) Notice: Subject to any disclaimer, the term of this patent is extended or adjusted under 35 U.S.C. 154(b) by 5 days.

(21) Appl. No.: 16/593,090

(22) Filed: Oct. 4, 2019

(65) Prior Publication Data
US 2020/0142016 A1    May 7, 2020

(30) Foreign Application Priority Data
Nov. 2, 2018  (JP) .............................. JP2018-207533

(51) Int. Cl.
*G01R 33/56* (2006.01)
*G01R 33/54* (2006.01)
(Continued)

(52) U.S. Cl.
CPC ....... *G01R 33/5608* (2013.01); *G01R 33/543* (2013.01); *G01R 33/5611* (2013.01);
(Continued)

(58) Field of Classification Search
CPC ............. G01R 33/5608; G01R 33/543; G01R 33/5611; G01R 33/546; G01R 33/5635;
(Continued)

(56) References Cited

U.S. PATENT DOCUMENTS 9,241,654 B2 * 1/2016 Edelman ................. A61B 5/004
2015/0346303 A1 * 12/2015 Hu ....................... G01R 33/5611
                                                                600/420
(Continued)

FOREIGN PATENT DOCUMENTS

JP    2016-123853 A    7/2016
JP    2018-007817 A    1/2018

OTHER PUBLICATIONS

"Location of Spatial Frequencies", Questions and Answers in MRI, 2021 <http://mriquestions.com/locations-in-k-space.html> (Year: 2021).*

(Continued)

*Primary Examiner* — Rishi R Patel
(74) *Attorney, Agent, or Firm* — Foley & Lardner LLP

(57) ABSTRACT

Provided is a new scheme for applying a CS technology in a technology for imaging a target tissue based on a difference from a reference image or a control image. In this way, an imaging time is shortened. A measurement unit of an MRI apparatus executes a first imaging sequence and a second imaging sequence having different contrasts for a target, and measures a nuclear magnetic resonance signal from a subject in each of the imaging sequences. In the second imaging sequence, under-sampling is performed, and a nuclear magnetic resonance signal having a small number of samples is measured. The image processing unit restores measurement data including a nuclear magnetic resonance signal obtained by under-sampling using compressed sensing. At this time, data restoration including a term for minimizing an L1 norm is performed for a difference image between an image obtained by execution of the first imaging sequence and an image obtained by execution of the second imaging sequence.

11 Claims, 10 Drawing Sheets

(51) Int. Cl.
*G01R 33/561* (2006.01)
*G01R 33/563* (2006.01)
*A61B 5/055* (2006.01)

(52) U.S. Cl.
CPC .......... *G01R 33/5635* (2013.01); *A61B 5/055* (2013.01); *G01R 33/546* (2013.01)

(58) Field of Classification Search
CPC ................ G01R 33/56509; G01R 33/561; A61B 5/055; A61B 5/0037; A61B 2576/026
See application file for complete search history.

(56) References Cited

U.S. PATENT DOCUMENTS

2016/0063739 A1\* 3/2016 Weizman .............. G06T 11/003
382/131
2016/0187446 A1 6/2016 Zhou
2017/0131376 A1\* 5/2017 Miyazaki ......... G01R 33/56316

OTHER PUBLICATIONS

"SENSE/ASSET", Questions and Answers in MRI, 2021 <http://mriquestions.com/senseasset.html> (Year: 2021).\*
Takashi Nishihara et al., "Selective TOF MRA using Beam Saturation pulse", Proc. ISMRM 2012, 2497.

\* cited by examiner

MAGNETIC RESONANCE IMAGING APPARATUS AND IMAGE PROCESSING APPARATUS

INCORPORATION BY REFERENCE

The present application claims priority from Japanese patent application JP-2018-207533 filed on Nov. 2, 2018, the content of which is hereby incorporated by reference into this application.

BACKGROUND OF THE INVENTION

Field of the Invention

The present invention relates to a magnetic resonance imaging (hereinafter referred to as MRI) apparatus, and more particularly to a technology (non-contrast angiographic imaging) for obtaining a desired blood vessel image without using a contrast agent.

Description of the Related Art

As non-contrast angiographic imaging using an MRI apparatus, there are known technologies, which are a technology (for example, Selective TOF MRA using Beam Saturation pulse. Takashi Nishimura, et al, Proc. ISMRM 2012, 2497 and JP-A-2018-7817) for obtaining an image in which only a desired blood vessel is depicted with high contrast by taking a difference between an image obtained by suppressing a signal from a predetermined blood vessel using a pre-saturation pulse and an image captured without using the pre-saturation pulse, and a technology (ASL: Arterial spin labeling) for labeling (putting in a distinguishable state) and imaging a spin in a blood flow to be observed in advance using an inversion pulse. In ASL, a difference image between an image obtained by labeling and a control image that is not labeled is acquired.

In the technology described in JP-A-2018-7817, there is a disclosed technology for selectively suppressing one of left and right carotid arteries, for example, in the case of imaging a blood vessel in a head, using a two-dimensional (2D) excitation pulse referred to as a Beam Saturation pulse (hereinafter referred to as a BeamSat pulse) as the pre-saturation pulse. By subtracting a three-dimensional (3D)-time of flight (TOF) image obtained by suppressing one of left and right blood vessels from a normal 3D-TOF image, it is possible to obtain separate left and right blood vessel images in a brain.

In angiographic imaging using such a pre-saturation pulse, in addition to normal 3D-TOF imaging, it is necessary to perform 3D-TOF imaging with BeamSat. Thus, in the case of obtaining left and right images, it takes three times more imaging time. In JP-A-2018-7817, it is proposed to reduce a frequency imaging time by reducing the number of encoding steps of 3D-k space data according to delicateness (spatial frequency) of the structure of a blood vessel to be observed.

Meanwhile, there is a proposed scheme of shortening an imaging time by applying a compressed sensing (CS) technology used in an image processing field to data under-sampled (collected as many as the number fewer than the specified number of samplings) by MRI and reproducing the data (JP-A-2016-123853). In the CS technology, when data is restored from observation data including an unknown, norm is optimized using sparsity of data. In a technology disclosed in JP-A-2016-123853, L1 norm is optimized for sparse space data obtained by performing sparse conversion such as wavelet conversion on an image reconstructed from under-sampled k-space data.

The technology disclosed in JP-A-2018-7817 is an effective scheme when a range of structures of a blood vessel to be observed is narrowed to some extent. However, when an observation target includes a fine blood vessel to a thick blood vessel, a sufficient time shortening effect may not be achieved.

In the CS technology, sparsity of the data used is an important factor for the accuracy of data restoration. Thus, in the technology described in JP-A-2016-123853, the accuracy is increased by a device for sparse conversion of observation data and a regularization term. However, an image (difference image) of blood vessel imaging accompanied by pre-saturation and labeling described above has not been studied.

SUMMARY OF THE INVENTION

An object of the invention is to shorten an imaging time by providing a new scheme for applying a CS technology in a technology for imaging a target tissue based on a difference from a reference image or a control image.

The invention solves the above problem by paying attention to the fact that portions of two images other than a portion remaining as a difference image are basically the same, and the difference image has sparsity.

In other words, the MRI apparatus of the invention includes a measurement unit that executes a first imaging sequence and a second imaging sequence having different contrasts for a target, and measures a nuclear magnetic resonance signal from a subject in each of the imaging sequences, a control unit that controls an operation of the measurement unit, and an image processing unit that creates an image of the target using measurement data including the nuclear magnetic resonance signal measured in each of the first imaging sequence and the second imaging sequence, in which the control unit controls the measurement unit to under-sample the second imaging sequence, the image processing unit includes a data restoration unit that restores the measurement data obtained by under-sampling using compressed sensing, a conversion unit that converts measurement data and image data, and a difference image computation unit that computes a difference between images obtained by different imaging sequences, and the data restoration unit performs data restoration to minimize an L1 norm for a difference image between an image obtained by execution of the first imaging sequence and an image obtained by execution of the second imaging sequence.

A function of the image processing unit of the invention described above may be realized by a calculator inside the MRI apparatus or realized in an image processing apparatus independent of an MRI apparatus that collects measurement data including a nuclear magnetic resonance signal.

That is, an image processing apparatus of the invention includes a receiving unit that receives first measurement data obtained by full sampling in an MRI apparatus and second measurement data obtained by under-sampling under a different imaging condition from an imaging condition of the first measurement data, a conversion unit that converts each of the first measurement data and the second measurement data into image data, and a data restoration unit that performs data restoration using compressed sensing. The data restoration unit performs data restoration of the second measurement data to minimize an L1 norm for difference data between first image data obtained by converting the first measurement data and second image data obtained by converting the second measurement data.

According to the invention, when the CS technology is applied, data restoration is performed using sparsity of a difference from a reference image or a control image. Since a difference image has higher sparsity than that of sparse space data used in CS calculation of a conventional MRI image reconstruction, it is possible to set a high double speed rate (thinning rate during under-sampling), and to shorten an imaging time of imaging that requires two types of imaging. At the same time, an accurately reproduced image, particularly a blood vessel image can be acquired.

BRIEF DESCRIPTION OF THE DRAWINGS

FIGS. 4A and 4B are diagrams illustrating examples of an imaging sequence used for measurement of the first embodiment, in which FIG. 4A is a 3D-TOF sequence not including a BeamSat pulse, and FIG. 4B is a 3D-TOF sequence including the BeamSat pulse;

FIGS. 8A and 8B are diagrams illustrating a resultant image obtained by actually performing image restoration of the first embodiment, in which FIG. 8A is a diagram illustrating a restored image according to the first embodiment, and FIG. 8B is a diagram illustrating an image of a reference example;

DETAILED DESCRIPTION OF THE INVENTION

Hereinafter, embodiments of an MRI apparatus of the invention will be described. First, an outline of the MRI apparatus common to the respective embodiments described later will be described.

Figure 1:
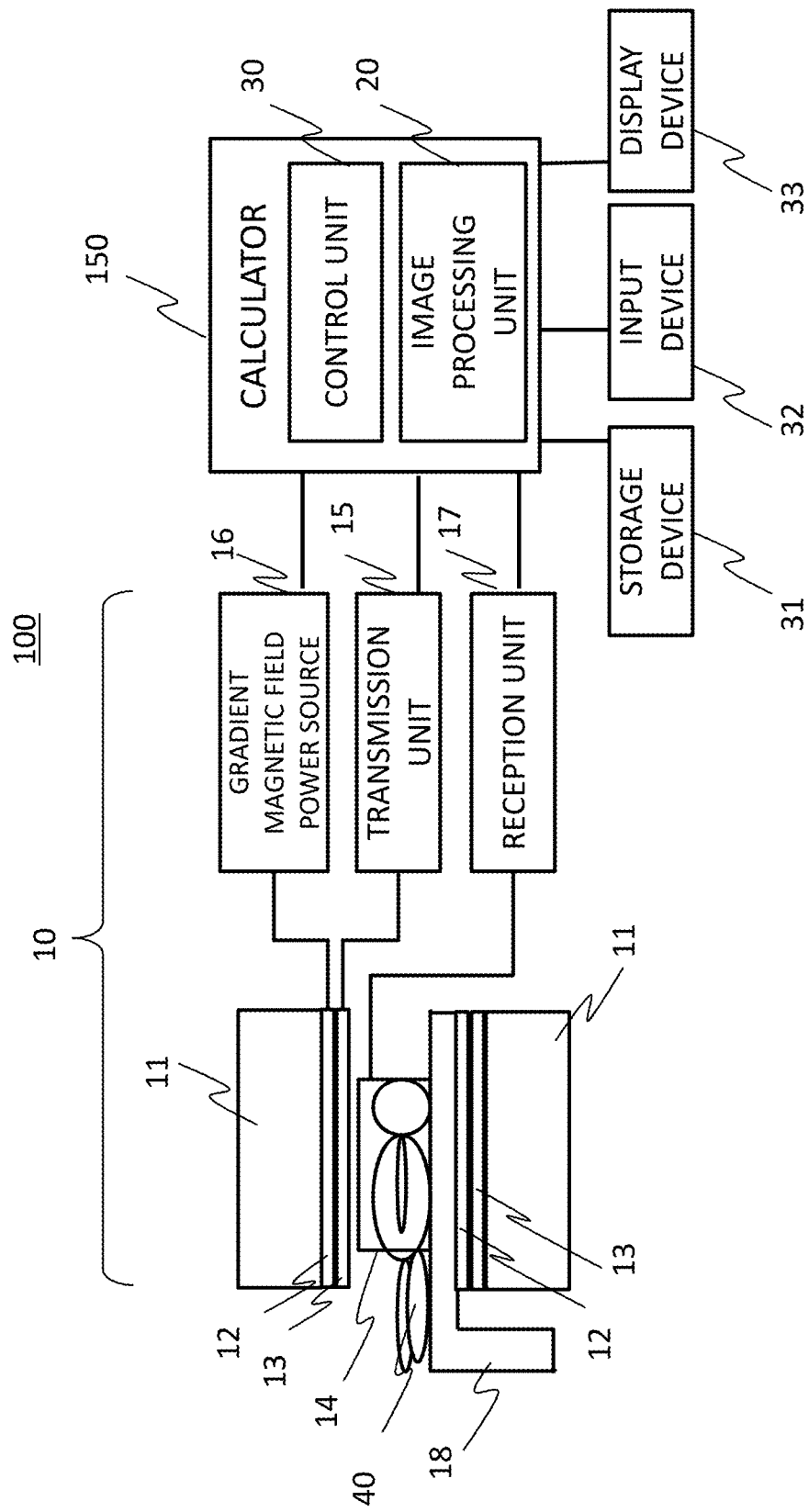
FIG. 1 is a block diagram illustrating an embodiment of an MRI apparatus of the invention.

As illustrated in FIG. 1, the MRI apparatus 100 according to the present embodiment roughly includes a measurement unit 10, an image processing unit 20, and a control unit 30 that controls the measurement unit 10 and the image processing unit 20. The measurement unit 10 is a part that excites spins of atoms contained in a tissue included in a subject and measures a nuclear magnetic resonance signal generated from the subject, and has the same configuration as that of a conventional MRI apparatus. Specifically, the measurement unit 10 includes a static magnetic field magnet 11, an RF coil (RF coil for transmission) 12 that transmits an RF pulse having a resonance frequency, a gradient magnetic field coil 13 that gives a magnetic field gradient to a static magnetic field, an RF coil (RF coil for reception) 14 that detects a nuclear magnetic resonance signal generated from the subject, a transmission unit 15 that transmits an RF signal to the RF coil for transmission 12 to operate the RF coil 12, a power source 16 for the gradient magnetic field coil 13, and a reception unit 17 that receives and detects a signal detected by the RF coil for reception 14. Further, a shim coil for correcting non-uniformity of the static magnetic field magnet 11 and a bed 18 for carrying the subject 40 into a static magnetic field space formed by the static magnetic field magnet 11 are provided.

The gradient magnetic field coil 13 includes three sets of coils that generate gradient magnetic fields in three axial directions, respectively, and it is possible to generate a gradient magnetic field pulse having a desired intensity in a desired direction by selecting a combination of gradient magnetic field pulses in three directions given by these three sets of gradient magnetic field coils 13. In this way, a region of the subject to be excited by the RF pulse can be selected, and position information along a desired direction can be given to a nuclear magnetic resonance signal generated from the subject.

Each element included in the measurement unit 10 is similar to that of a well-known apparatus, and various well-known modifications and improvements may be added. In this specification, detailed description is omitted unless particularly necessary in relation to the invention.

Figure 2:
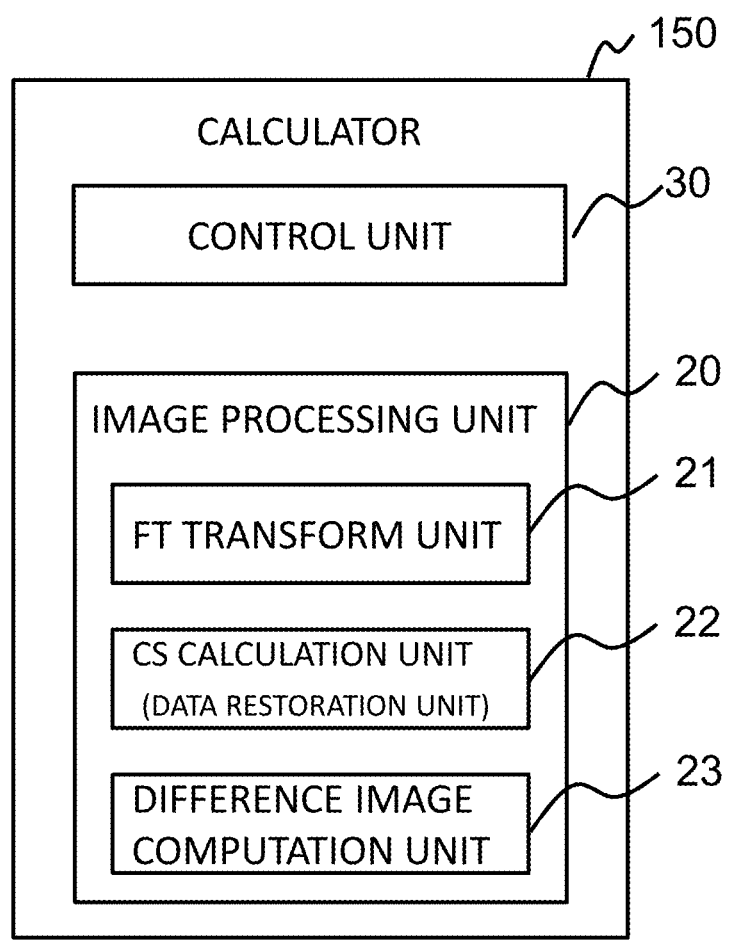
FIG. 2 is a block diagram mainly illustrating details of a measurement unit of the MRI apparatus.

The image processing unit 20 performs various calculations and image processing on measurement data (nuclear magnetic resonance signal) acquired by the measurement unit 10 to create an image related to the subject. As illustrated in FIG. 2, the image processing unit 20 includes an FT transform unit 21 that performs transformation such as Fourier transform or inverse Fourier transform, a CS calculation unit (data restoration unit) 22 that performs CS computation, and a difference image computation unit 23 that creates a difference image by calculating a difference between images, etc. A function of the image processing unit 20 can be realized by a computer including a CPU or a GPU. In addition, some or all of the functions may be realized by hardware such as an application specific integrated circuit (ASIC) or a field programmable gate array (FPGA). In an example illustrated in FIG. 2, the image processing unit 20 is realized by a calculator 150 including a CPU and a GPU together with the control unit 30 described later.

The control unit 30 controls operations of respective parts of the measurement unit 10 and the image processing unit 20 described above when the calculator 150 uploads and executes a program for control or calculation. Separately from the calculator 150, the control unit 30 may include a sequencer that particularly controls the measurement unit 10.

The control unit 30 (calculator 150) may further include an input device 32 for inputting a condition and a parameter necessary for calculation by the calculator 150, a display device 33 that displays a calculation result, a graphical user interface (GUI), etc., a storage device 31 that stores data necessary for control or calculation of the control unit 30, data in the middle of calculation, or a calculation result, etc. Specifically, the control unit 30 controls operations of the transmission unit 15, a gradient magnetic field power source 16, the reception unit 17, etc. so that application of an RF pulse and a gradient magnetic field pulse and reception of a nuclear magnetic resonance signal are performed according to a predetermined imaging sequence. Referring to imaging sequence, by an imaging method, various pulse sequences are prepared in advance and stored in the storage device 31. When the user selects an inspection protocol including a predetermined pulse sequence or the pulse sequence via the input device 32, and sets an imaging condition such as an imaging parameter for executing the pulse sequence, a desired imaging sequence can be executed. In addition, the control unit 30 controls an operation of the image processing unit 20.

Hereinafter, a specific embodiment of the control of the control unit 30 will be described. In the following embodiment, a case where a target site (target) for imaging is a blood vessel will be described. However, the target is not limited to the blood vessel.

FIRST EMBODIMENT

In the present embodiment, the control unit 30 controls the measurement unit 10 to execute two 3D-TOF sequences as a angiographic imaging sequence. One is a 3D-TOF sequence (first imaging sequence) not including a pre-saturation pulse, and the other one is a 3D-TOF sequence (second imaging sequence) including a pre-saturation pulse. For example, the pre-saturation pulse is a 2D excitation BeamSat pulse that excites a predetermined columnar region. The image processing unit 20 performs calculation between two types of images obtained by these two imaging sequences, and creates an image obtained with high contrast by a blood vessel other than apart suppressed by the pre-saturation pulse.

A flow from imaging to image creation in the present embodiment will be described with reference to FIG. 3.

First, an imaging sequence and an imaging condition such as an imaging parameter are set, and measurement is started (S301). In accordance with the set condition, the measurement unit 10 executes two imaging sequences (3D-TOF pulse sequences) and acquires measurement data for each of the sequences.

Figure 4:
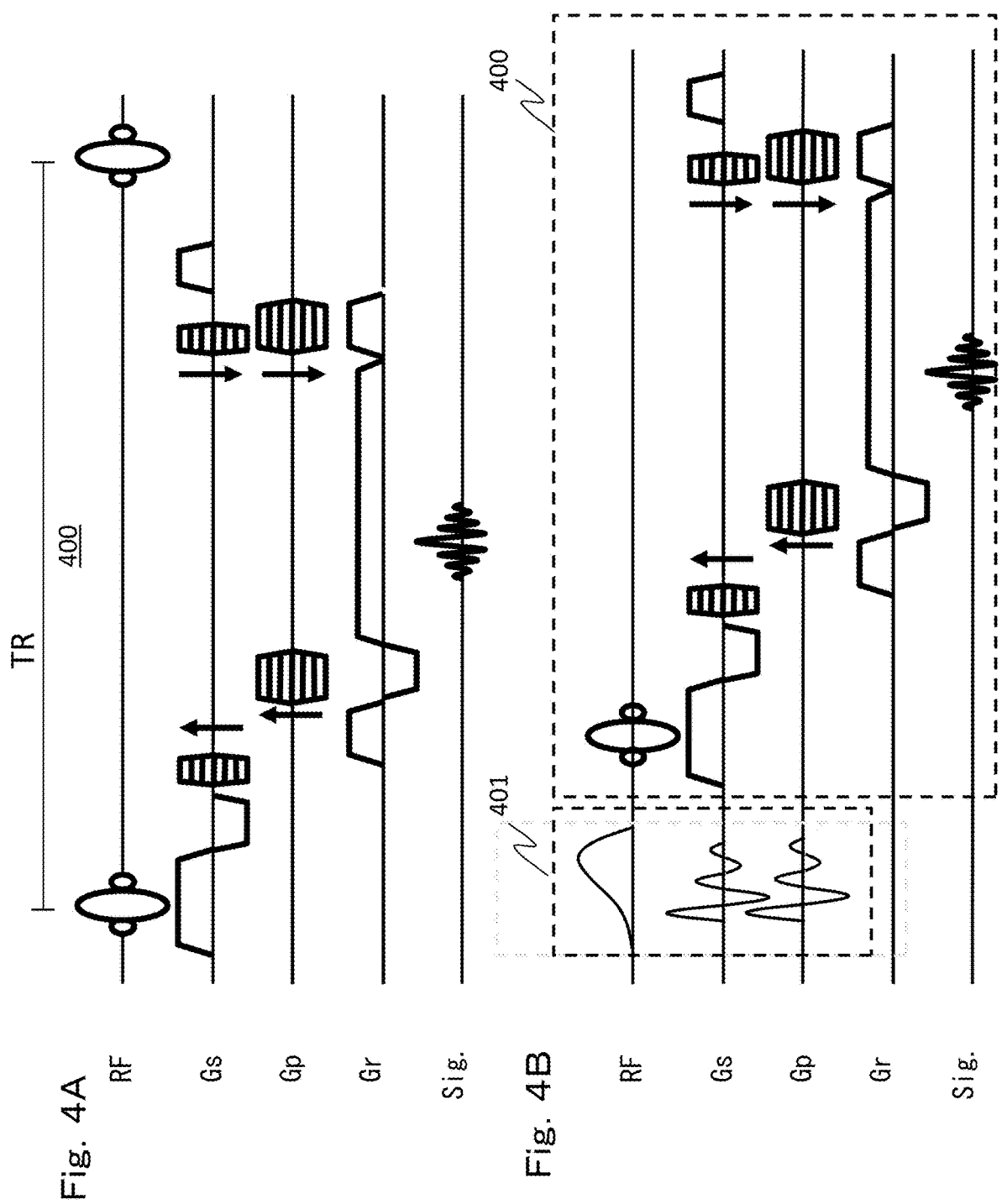

The 3D-TOF pulse sequence is a sequence that depicts a blood flow spin with high contrast using an inflow effect. As illustrated in FIG. 4A, the 3D-TOF pulse sequence applies an RF pulse (RF) for excitation together with a gradient magnetic field pulse (Gs). After exciting a desired region, a gradient magnetic field pulse for encoding is applied in each of two axial directions (slice encoding direction Gs and phase encoding direction Gp in the figure), and a read gradient magnetic field Gr whose polarity is reversed is applied to measure an echo signal Sig. Thereafter, a gradient magnetic field pulse for rephase is applied. While one of a slice encoding gradient magnetic field Gs and a phase encoding gradient magnetic field Gp is made different, such a sequence is repeated with a repetition time TR until a predetermined number of encoding steps for each of the encoding gradient magnetic fields is obtained. Finally, 3D measurement data is obtained. A k-space scanning method determined by a combination of the gradient magnetic fields Gs and Gp is not particularly limited, and it is possible to adopt a known scanning method such as Cartesian scan for measuring k-space in parallel along an axis, radial scan for radially measuring k-space, spiral scan for spirally measuring k-space, etc.

In an imaging sequence of FIG. 4B, prior to a 3D-TOF pulse sequence 400 described above, a BeamSat pulse 401 including a combination of an RF pulse for 2D excitation and a gradient magnetic field pulse is applied. The BeamSat pulse is a combination of an RF pulse whose intensity changes asymmetrically and oscillating gradient magnetic fields Gx and Gy in two axial directions as illustrated by being surrounded by a dotted square on a left side. A columnar region along an arbitrary direction can be selected by selecting axes of the oscillating gradient magnetic fields Gx and Gy, and a diameter of a columnar region can be controlled by application amounts of the oscillating gradient magnetic fields. FIG. 4B illustrates a case where axes Gx and Gy of the gradient magnetic fields correspond to Gs and Gp, respectively.

Figure 5:
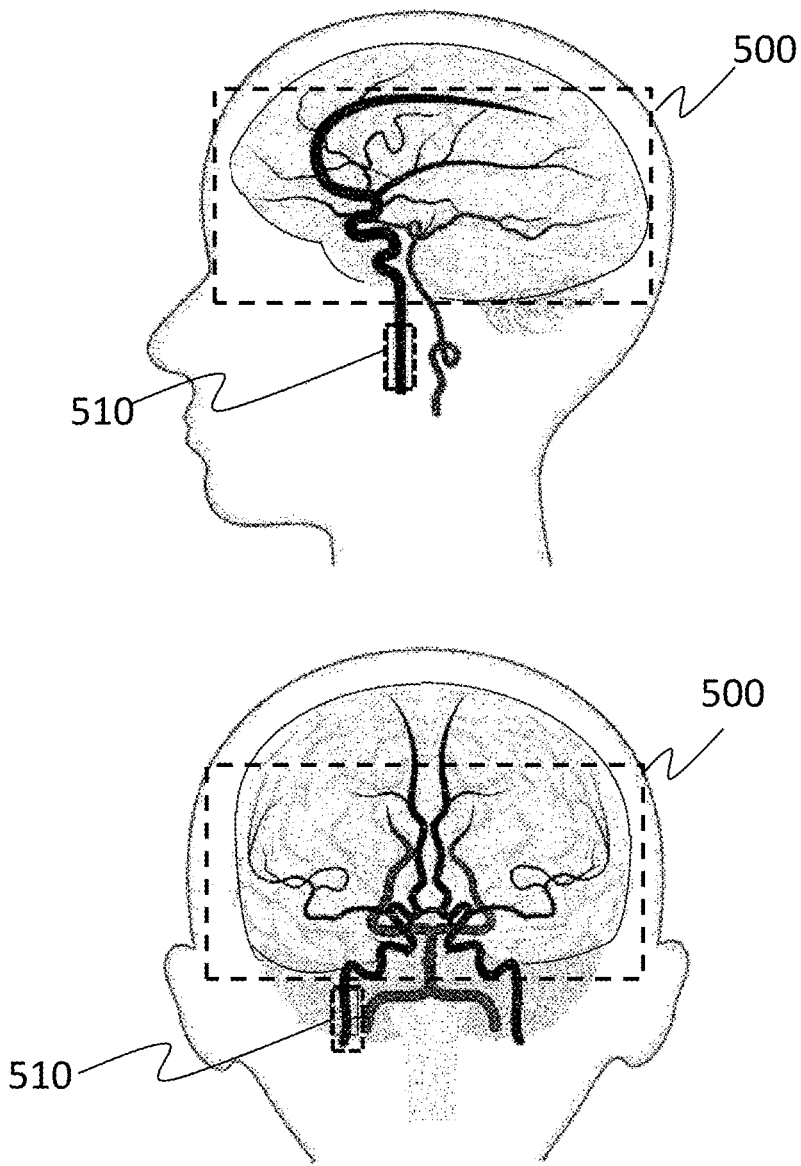
FIG. 5 is a diagram illustrating a relationship between a target region and a pre-saturation region.

In the present embodiment, when a running state of a blood vessel in a brain is set as an imaging target, one of a right carotid artery and a left carotid artery is selected, and a blood flow spin in a selected region is saturated in advance. For example, as illustrated in FIG. 5, the axis of the gradient magnetic field is determined so that a columnar region 510 passes through one of the right carotid artery and the left carotid artery and does not overlap with a region 500 to be imaged. Referring to determination of the axis of the gradient magnetic field, for example, a scout image obtained by high-speed imaging a head of the subject with low resolution may be displayed on the display device 33 so that the user designates a desired suppression region. Alternatively, after the imaging region 500 is set, a predetermined region empirically determined in relation to the imaging region 500 may be automatically set.

Figure 6B:
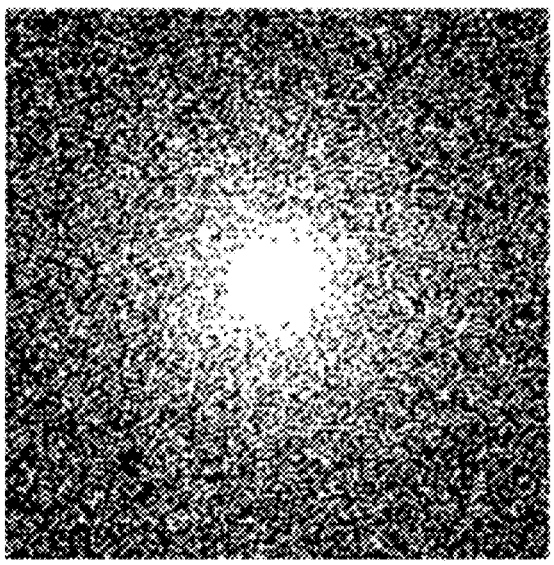
FIGS. 6A and 6B are diagrams, each of which illustrates an example of under-sampling of k-space.
Figure 6A:
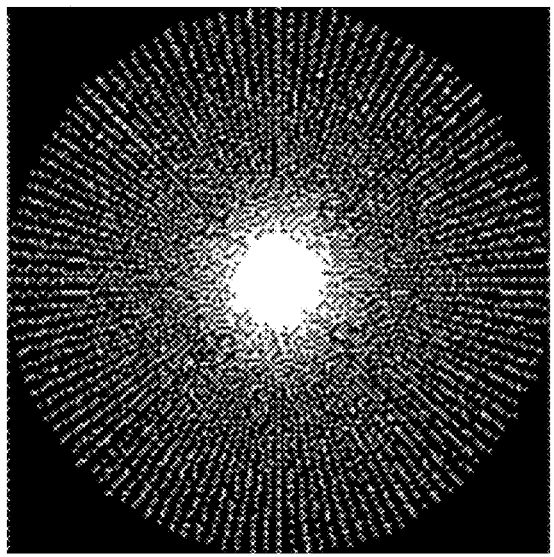

The 3D-TOF pulse sequence 400 following such a pre-saturation pulse is basically the same as the 3D-TOF pulse sequence of FIG. 4A. However, in a case where the BeamSat pulse is not applied, the number of encoding steps in the phase encoding direction and slice encoding direction is the number of encoding steps not causing aliasing in the FOV set as the imaging parameter (full sampling). On the other hand, in the pulse sequence of FIG. 4B, sampling is performed with a smaller number of encoding steps (under-sampling). There is no particular limitation on a method of thinning out data. However, for example, as illustrated in FIGS. 6A and 6B, in a radial scan in which k-space is radially sampled, a sampling angle may be thinned out or thinned out in a dotted manner. Further, in an orthogonal scan, it is possible to obtain a predetermined thinning rate by sampling so as to decrease the sampling density from a center of k-space toward a periphery in the phase encoding direction or the slice encoding direction. In this way, in the 3D-TOF pulse sequence with the BeamSat pulse, a measurement time can be shortened almost in proportion to the thinning rate by under-sampling. The thinning rate can be designated by the user using an imaging parameter referred to as a double speed rate corresponding to a reciprocal of the thinning rate.

Any one of the 3D-TOF pulse sequence (hereinafter referred to as a first imaging sequence) illustrated in FIG. 4A and the 3D-TOF pulse sequence with the BeamSat pulse (hereinafter referred to as a second imaging sequence) illustrated in FIG. 4B may be executed in advance, or the second imaging sequence may be appropriately interposed between repeated first imaging sequences corresponding to the repetition number.

Finally, in both imaging sequences, echo signals of the set number of encoding steps (multiple times the number of additions when there is addition) are collected, and measurement (S301) is completed.

Subsequently, the image processing unit 20 creates respective images using 3D-k-space data including the echo signals, takes a difference between two images, and creates a difference image (S302 to S305). In processing by the image processing unit 20, it may not be necessary to wait for all measurements to be completed. For example, when echo signal collection of one imaging sequence (for example, 3D-TOF pulse sequence without BeamSat pulse) out of two imaging sequences is completed, it is possible to perform image reconstruction of k-space data at that time.

In step S302, the FT transform unit 21 performs 3D-inverse Fourier transform on the 3D-k-space data obtained in the first imaging sequence to obtain 3D-image data (image 1).

In step S303, the CS calculation unit 22 restores the 3D-k-space data obtained by the under-sampled second imaging sequence. The CS calculation unit 22 restores data according to the following equation.

[Equation 1]

$$\operatorname{argmin}(\|F_u I_{wSAT} - y\|_2^2 + \lambda |I_{woSAT} - I_{wSAT}|_1) \qquad (1)$$

In Equation (1), $I_{woSAT}$ and $I_{wSAT}$ correspond to an image (image 1) obtained by the first imaging sequence and an image (image 2) obtained by the second imaging sequence, respectively, $F_u$ represents the Fourier transform (conversion from image data into measurement space data), and y denotes 3D-k-space data (measurement data) obtained in the second imaging sequence. $\lambda$ is a coefficient of a second term.

In data restoration represented by the Equation (1), when a difference (L2 norm) between the measurement data y and the restored data is minimized, a term in which an L1 norm of a difference between the image 1 and the image 2 is minimized is added as a regularization term.

Figure 7:
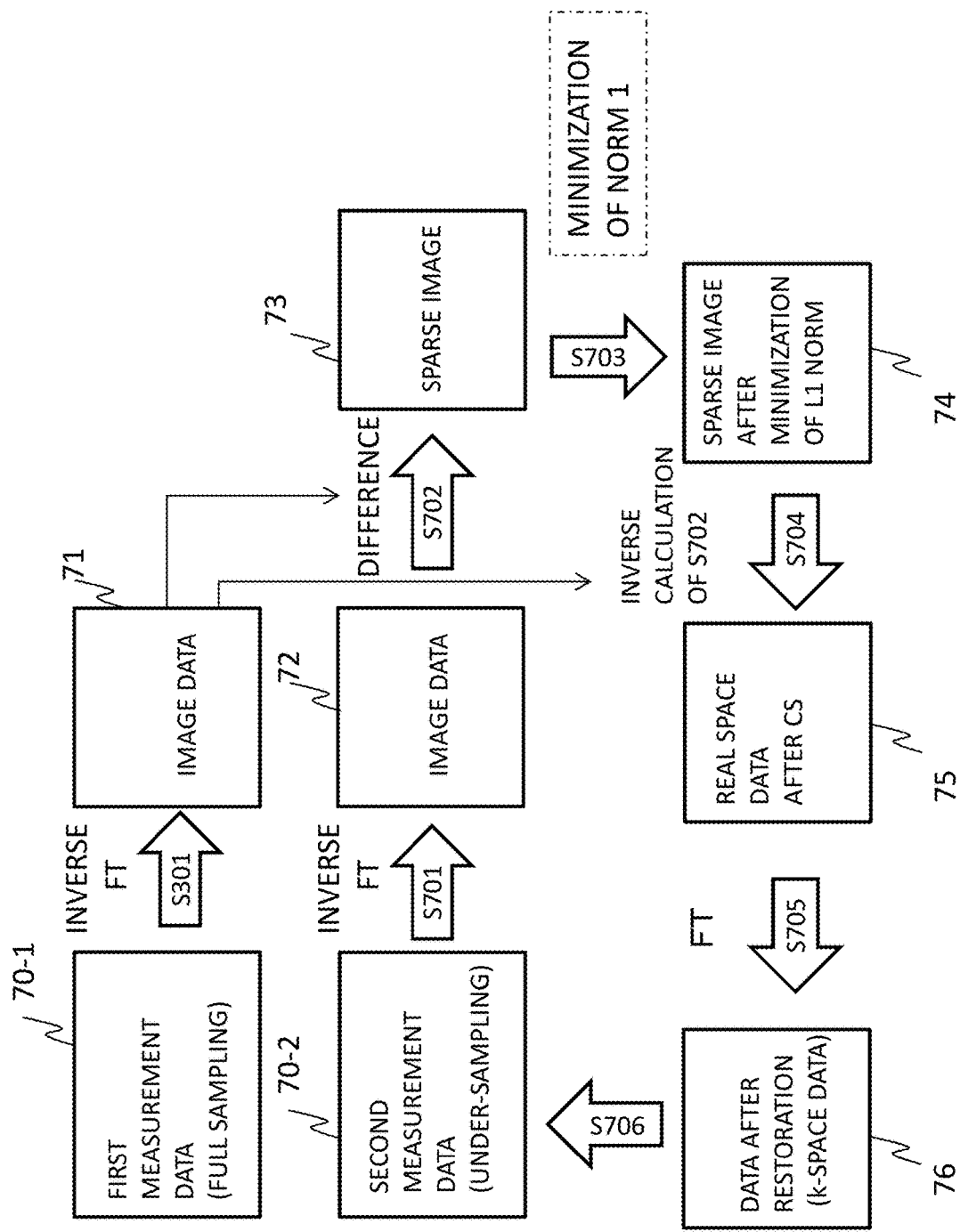
FIG. 7 is a diagram illustrating a concept of image restoration of the first embodiment.

Specific processing for data restoration is repetitive calculation illustrated in FIG. 7. That is, measurement data (y) 70-2 under-sampled in the second imaging sequence is subjected to inverse Fourier transform (S701) to obtain real space data ($I_{wSAT}$) 72. Subsequently, a difference between the real space data 72 and the image data ($I_{woSAT}$) 71 of the first imaging sequence obtained in step S302 is obtained (S702) to obtain difference data 73. The L1 norm is minimized for the difference data 73 (S703).

Inverse calculation of S702 is performed on difference data 74 after the L1 norm is minimized (S704). That is, when the difference data 73 is 61 (=image 1−image 2) and the processed difference data 74 is 62, the inverse calculation is calculation of subtracting 62 from the image 1 (image 1−62). Real space data 75 obtained in this way is Fourier-transformed (S705) and returned to k-space data 76 ($F_u I_{wSAT}$).

In subsequent repetition, the k-space data 76 is replaced with the measurement data 71 and the same calculation is performed. The repetition may be performed a predetermined number of times, or a threshold for determining an end of the data 76 may be set, and the repetition may be terminated when the threshold is reached. Through the above processing, restored k-space data, that is, k-space data (data after restoration) corresponding to the fully sampled k-space data in the second imaging sequence is obtained.

Subsequently, in step S304, the FT transform unit 21 performs 3D-inverse Fourier transform on the restored k-space data to obtain 3D-image data. Finally, in step S305, a difference between the image (image 1) obtained in the first imaging sequence and the image obtained in step S304 is taken to create a blood vessel image. When the BeamSat pulse of the second imaging sequence is, for example, a pre-saturation pulse that suppresses a blood flow spin signal of the left carotid artery, a signal from a blood flow flowing from the left carotid artery to the right half of the brain is suppressed, and a blood vessel image in which a left blood vessel of the brain is depicted with high contract is obtained. The reverse is similar thereto.

The obtained image data is stored in, for example, the storage device 31 and displayed on the display device 33 as a display image (S306).

When a plurality of small receiving coils having different sensitivity distributions are used as the RF coil for reception 14, thinning imaging may be performed at a thinning rate corresponding to the number of small receiving coils in an imaging step (S301), and calculation by a parallel imaging method using the sensitivity distributions of the receiving coils may be performed to reconstruct the image at the time of converting the measurement data into the image data in an image reconstruction step (S302 and S701).

EXAMPLE

Figure 8B:
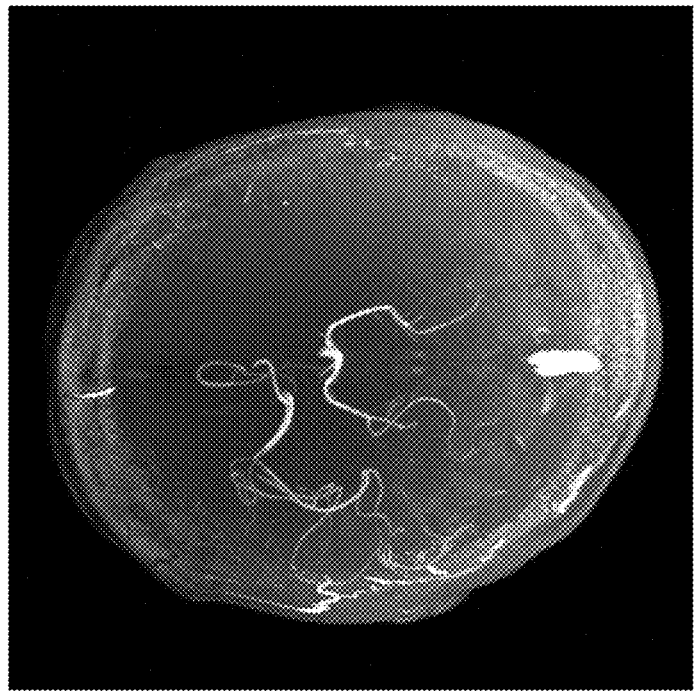
Figure 8A:
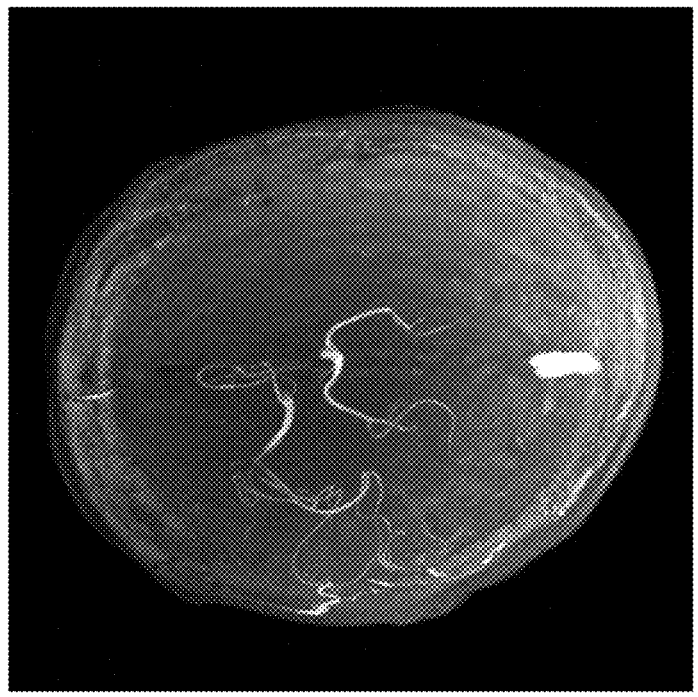

FIG. 8A illustrates a difference image created by performing measurement not using BeamSat and measurement using BeamSat using the 3D-TOF pulse sequence illustrated in FIGS. 4A and 4B. An imaging condition of the 3D-TOF pulse sequence was set to FOV: 220 mm, TR: 23.8 msec, TE: 3.3 msec, FA: 15 degrees, number of slice encodings: 60, number of phase encodings: 224, and a thinning rate of the second imaging sequence with BeamSat was set to ⅕. A difference between an image obtained by restoring measurement data acquired by the second imaging sequence according to the above Equation (1) with the repetition number of 20 and performing image reconstruction and an image obtained by measurement without BeamSat and obtained by full sampling thereof is an image illustrated in FIG. 8A.

As a reference example, FIG. 8B illustrates a difference image in the case of full-sampling the second imaging sequence. As can be understood from comparison with the image of the reference example, in the image of FIG. 8A, blood vessels on one side of the brain are depicted with substantially the same contrast as that in the case of full sampling. In addition, referring to the imaging time, while the imaging time of the image of FIG. 8B was 5 minutes 20 seconds, the imaging time of the image of FIG. 8A was 1 minute 4 seconds. In this way, it was possible to reduce the imaging time by about 4 minutes 16 seconds.

As described above, according to the present embodiment, at the time of creating a blood vessel image by taking a difference between an image acquired by a 3D-TOF sequence with pre-saturation and an image acquired by a 3D-TOF sequence without pre-saturation, the 3D-TOF sequence with pre-saturation is under-sampled, and measurement data thereof is restored using the CS technology. Thus, it is possible to greatly shorten an imaging time as a whole. In addition, in application of the CS technology, using the fact that the image acquired by the 3D-TOF sequence with pre-saturation and the image acquired by the 3D-TOF sequence without pre-saturation are almost equal to each other except for a blood vessel portion, and sparsity of a difference image thereof is high, the L1 norm in the sparse space is minimized. Thus, it is possible to increase the double speed rate and the accuracy of data restoration, and to obtain a highly accurate difference image at high speed.

<Modification 1>

In the first embodiment, the CS calculation is performed using the sparsity of the difference image, and thus data conversion to a sparse space that is essential in normal CS calculation, such as wavelet conversion, is unnecessary. However, in addition to a term, of Equation (1), it is possible to add a sparse conversion term, a term that minimizes a total variation TV on the image, etc. Only one of these terms may be added, or both terms may be added. For example, when both terms are added, Equation (1) becomes the following Equation (2).

[Equation 2]

$$\operatorname{argmin}(\|F_u I_{wSAT} - y\|_2^2 + \lambda 1 |I_{woSAT} - I_{wSAT}|_1 + \lambda 2 |\Psi I_{wSAT}|_1 + \lambda 3 |TV(I_{wSAT})|_1) \qquad (2)$$

In Equation (2), a third term is a term that minimizes the L1 norm of the sparse space data after being transformed by the wavelet transform Ψ, etc., and a fourth term is a term that minimizes the total variation (TV) on the image or the L1 norm thereof. Each of $\lambda_1$ to $\lambda_3$ is a coefficient for determining a weight of a regularization term.

By increasing the normalization term, a calculation time becomes longer. However, the accuracy of restoration can be further increased.

<Modification 2>

Figure 9:
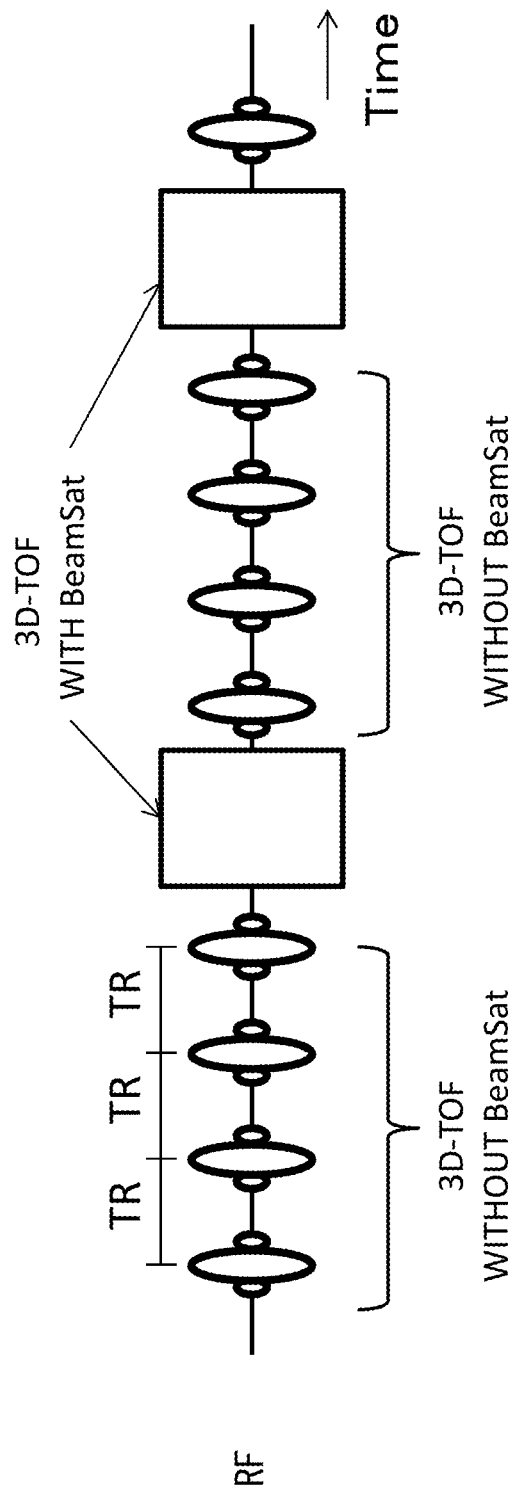
FIG. 9 is a diagram illustrating a time chart of execution of an imaging sequence in Modification 2 of the first embodiment.

In the first embodiment, the order of performing the first imaging sequence and the second imaging sequence is not particularly limited. However, the second imaging sequence may be executed during repetition of the first imaging sequence. FIG. 9 illustrates an example of measurement for executing the second imaging sequence in a nested manner during execution of the first imaging sequence. Note that TR illustrated in FIG. 9 corresponds to TR of the imaging sequence illustrated in FIGS. 4A and 4B. FIG. 9 illustrates only the RF pulse in the pulse sequence of FIGS. 4A and 4B and omits other pulses and signal collection.

In the example of FIG. 9, in each slice encoding, one TR of the second imaging sequence is inserted every N (here, four) TRs of the first imaging sequence, and one TR is executed in the second imaging sequence with respect to N TRs in the first imaging sequence. The repetition number of the continuous first imaging sequence may be changed according to the double speed number of the second imaging sequence, and the repetition number of the second imaging sequence inserted between repetitions (TR) of the first imaging sequence may be greater than one.

According to this modification, since the first imaging sequence and the second imaging sequence are executed within substantially the same measurement time, it is possible to reduce an influence of body movement between the two imaging operations, and to prevent degradation of the difference image due to body movement.

Second Embodiment

In the first embodiment, angiographic imaging is performed using a 3D-TOF sequence. However, in the present embodiment, an ASL sequence is used as the imaging sequence. In the ASL sequence, a preliminary pulse that makes it possible to distinguish a blood flow spin flowing through a specific blood vessel in advance is applied, an image is acquired by executing a angiographic imaging sequence, a difference from an image (control) obtained in the same angiographic imaging sequence executed without applying the preliminary pulse is taken, and a blood vessel image is created. For example, in the case of creating a cerebral blood flow image, a region including a carotid artery is selected, a preliminary pulse for labeling a spin is applied, a brain is selected after waiting for a time for the blood flow spin labeled by the preliminary pulse to reach the brain, and the angiographic imaging sequence is executed. As the preliminary pulse, an IR pulse for inverting spin is generally used. Selection of a region to be labeled may correspond to slice selection of a region including the carotid artery or columnar region selection for selecting only the carotid artery.

As the angiographic imaging sequence, a fast spin echo (FSE) sequence can be adopted. Moreover, it is possible to adopt a similar TOF sequence to that of the first embodiment.

Figure 3:
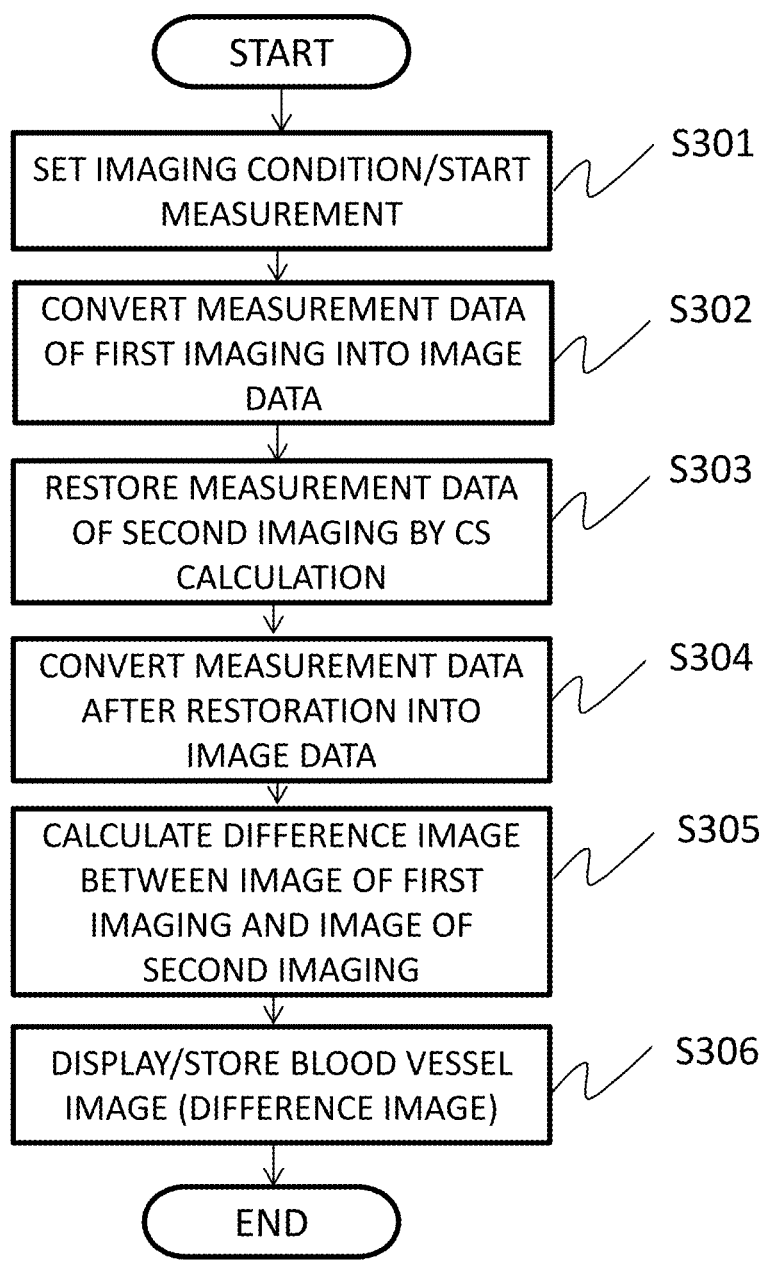
FIG. 3 is a flowchart illustrating an outline of measurement and image restoration of a first embodiment.

In the present embodiment, a flow of imaging is similar to that of the steps of the first embodiment illustrated in FIG. 3. The ASL sequence (imaging sequence with a preliminary pulse) is under-sampled (S301). Using a difference between an image obtained by the ASL sequence and a control image, measurement data of the ASL sequence is restored to minimize the L1 norm of the difference by the CS calculation (S302 and S303). An image of the ASL sequence (image after restoration) is created using the restored measurement data, and a difference from the control image is taken to obtain a blood vessel image (S304 and S305). Since the difference data used for the CS calculation is highly sparse data as in the first embodiment, an excellent restoration result can be obtained in the CS calculation.

According to the present embodiment, since it is necessary to wait for the arrival time after applying the preliminary pulse, the measurement time can be shortened by under-sampling the ASL sequence that increases the measurement time, and a blood vessel image having excellent image quality can be obtained by performing restoration of the measurement data by CS calculation using a difference from the control image.

In the present embodiment, it is possible to adopt a modification similar to the modifications of the first embodiment. In addition, in the first embodiment and the second embodiment, a description has been given of imaging using a pre-saturation pulse and imaging using an ASL pulse (preliminary pulse) as examples of imaging for creating a difference image. However, the invention is not limited thereto. When a difference between images obtained by two imaging operations has high sparsity and imaging finally obtains a difference image, the invention can be applied.

<Embodiment of Image Processing Apparatus>

Figure 10:
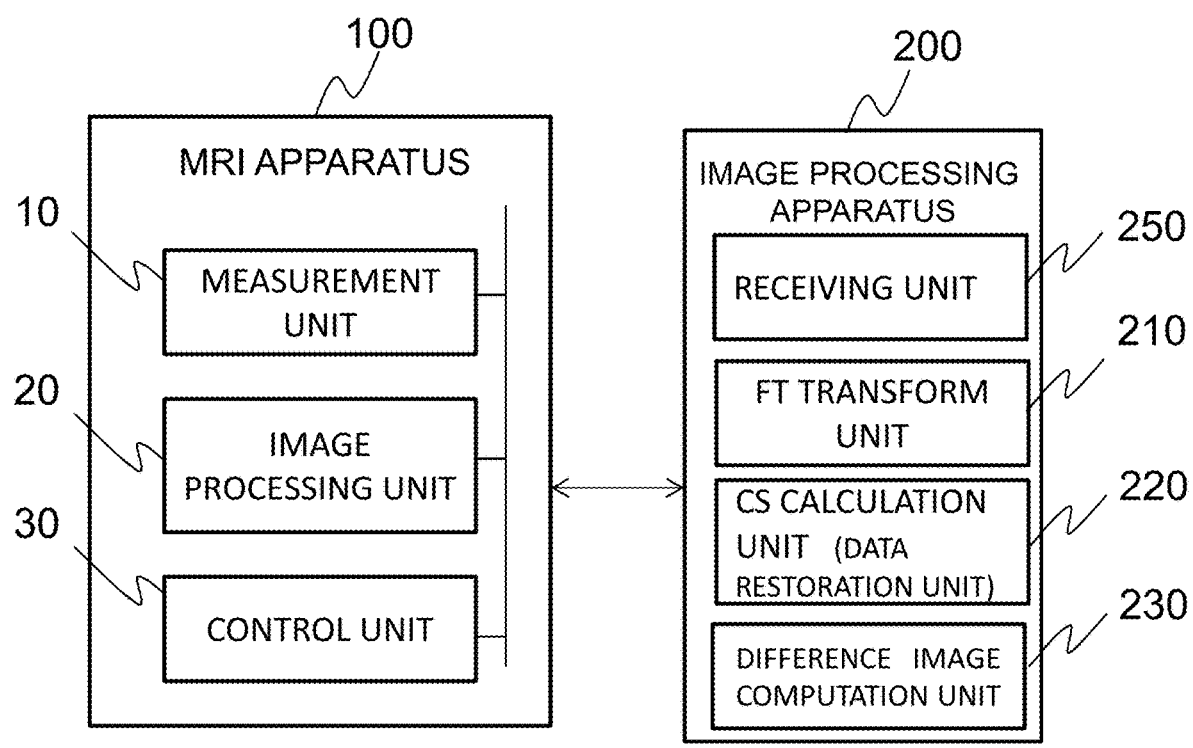
FIG. 10 is a diagram illustrating an embodiment of an image processing apparatus of the invention.

Even though the embodiment of the MRI apparatus of the invention has been described above, some or all of the functions performed by the image processing unit 20 in the MRI apparatus of FIG. 1 may be realized in an image processing apparatus independent of the MRI apparatus, and a system including the MRI apparatus 100 and the image processing apparatus 200 is included in the invention. FIG. 10 illustrates an example of the image processing apparatus.

The image processing apparatus 200 fetches measurement data measured by the MRI apparatus 100, performs image reconstruction, and outputs image data. For realizing this function, the image processing apparatus 200 includes a receiving unit 250 that receives data from the MRI apparatus 100, and further includes an FT transform unit 210, a CS calculation unit (data restoration unit) 220, and a difference image computation unit 230 similarly to the image processing unit 20 of FIG. 2. Functions of these units are similar to those of the image processing unit 20 described above. The image processing unit 20 of the MRI apparatus 100 in this embodiment has a similar function to that of image processing of a general MRI apparatus. However, the image processing unit 20 may have a function of the image processing apparatus 200.

FIG. 10 illustrates the image processing apparatus that realizes all functions of the image processing unit 20 of FIG. 2. However, only some of the functions of the image processing unit 20, for example, the FT transform unit 210 and the CS calculation unit 220 may be realized by the image processing apparatus 200, measurement data restored by the CS calculation unit 220 may be sent to the MRI apparatus 100, and image reconstruction and processing of a difference, etc. may be performed in the image processing unit 20 of the MRI apparatus.

In such a system, for data exchange between the MRI apparatus 100 and the image processing apparatus 200, it is possible to employ a known unit such as a wired or wireless data transmission/reception unit or a portable medium. In addition, the image processing apparatus 200 may be constructed in a cloud, etc., or may include a plurality of CPUs. As described above, by realizing a predetermined calculation function using a modality different from that of the MRI apparatus, a degree of freedom of the user can be increased and the load on the calculator in the MRI apparatus can be reduced.

What is claimed is:

1. A magnetic resonance imaging (MRI) apparatus comprising:
   a measurement unit that executes a first imaging sequence and a second imaging sequence having different contrasts for a target, the measurement unit configured to measure a nuclear magnetic resonance signal from a subject in each of the imaging sequences;
   a control unit that controls an operation of the measurement unit;
   an image processing unit that creates an image of the target using measurement data including the nuclear magnetic resonance signal measured in each of the first imaging sequence and the second imaging sequence;
   wherein the control unit controls the measurement unit such that the measurement unit under-samples the measurement data obtained during the second imaging sequence;
   wherein the image processing unit includes:
      a data restoration unit that restores the measurement data obtained by under-sampling using compressed sensing;
      a conversion unit that converts measurement data and image data; and
      a difference image computation unit that computes a difference between images obtained by different imaging sequences; and
   wherein the data restoration unit performs data restoration to minimize an L1 norm for a difference image between an image obtained by execution of the first imaging sequence and an image obtained by execution of the second imaging sequence,
   wherein echo signals of a set number of encoding steps are collected in both of the first imaging sequence and the second imaging sequence, the echo signals being included within the image data;
   wherein the first imaging sequence is a time of flight (TOF) sequence that does not include a pre-saturation pulse, and the second imaging sequence is a TOF sequence that includes a pre-saturation pulse; and
   wherein the control unit controls the measurement unit to alternately measure a plurality of repetition times of the first imaging sequence and measure one or more repetition times of the second imaging sequence, wherein a number of the plurality of repetition times is changed based on a double speed number of the second imaging sequence.

2. The MRI apparatus according to claim 1, wherein the control unit controls the measurement unit to fully sample the measurement data obtained during the first imaging sequence.

3. The MRI apparatus according to claim 1, wherein the data restoration unit performs data reproduction using compressed sensing according to Equation (1), specified as follows:

$$\operatorname{argmin}(\|F_u I_{wSAT} - y\|_2^2 + \lambda |I_{woSAT}|_1) \quad (1);$$

wherein $I_{woSAT}$ and $I_{wSAT}$ respectively represent an image obtained by the first imaging sequence and an image obtained by the second imaging sequence, $F_u$ represents a Fourier transform, y denotes measurement data obtained in the second imaging sequence, and $\lambda$ is a coefficient.

4. The MRI apparatus according to claim 3, wherein Equation (1) further includes at least one of a term that minimizes an L1 norm of a sparse transformation space and a term that minimizes a total variation.

5. The MRI apparatus according to claim 1, wherein the target is a head blood vessel of the subject, and the pre-saturation pulse is a pulse for selectively exciting a columnar region.

6. The MRI apparatus according to claim 1, wherein the first imaging sequence and the second imaging sequence correspond to non-contrast angiographic imaging sequences, and the second imaging sequence includes a pulse for labeling the target.

7. An image processing apparatus for performing image reconstruction using compressed sensing, the image processing apparatus comprising:
   a receiving unit that receives first measurement data obtained by full sampling in an MRI apparatus and second measurement data obtained by under-sampling under a different imaging condition from an imaging condition of the first measurement data;
   a conversion unit that respectively converts the first measurement data and the second measurement data into first image data and second image data; and
   a data restoration unit that restores under-sampled measurement data;
   wherein the data restoration unit performs a calculation using compressed sensing to minimize an L1 norm for difference data, the difference data determined between the first image data and the second image data;
   wherein each of the first measurement data and the second measurement data are respectively obtained from a first imaging sequence and a second imaging sequence, and
   wherein echo signals of a set number of encoding steps are collected in both of the first imaging sequence and the second imaging sequence, the echo signals being included within at least one of the first image data and the second image data;
   wherein the first imaging sequence is a time of flight (TOF) sequence that does not include a pre-saturation pulse, and the second imaging sequence is a TOF sequence that includes a pre-saturation pulse; and
   wherein a control unit controls a measurement unit to alternately measure a plurality of repetition times of the first imaging sequence and measure one or more repetition times of the second imaging sequence, wherein a number of the plurality of repetition times is changed based on a double speed number of the second imaging sequence.

8. The image processing apparatus according to claim 7, further comprising:
   a difference image computation unit that obtains a difference between image data obtained by converting the second measurement data restored by the data restoration unit and the first image data, and computes a difference image.

9. The MRI apparatus according to claim 1, wherein the measurement unit comprises a radiofrequency (RF) coil for detecting a signal generated from a subject, the RF coil comprising a plurality of receiving coils having different sensitivity distributions, and wherein the measurement unit executes thinning imaging at a thinning rate corresponding to a number of receiving coils.

10. The MRI apparatus according to claim 9, wherein the sensitivity distributions are used to reconstruct the image at a time of converting the measurement data into the image data.

11. The MRI apparatus according to claim 1, wherein the second imaging sequence is executed during a repetition of the first imaging sequence.

* * * * *